Figure 1:
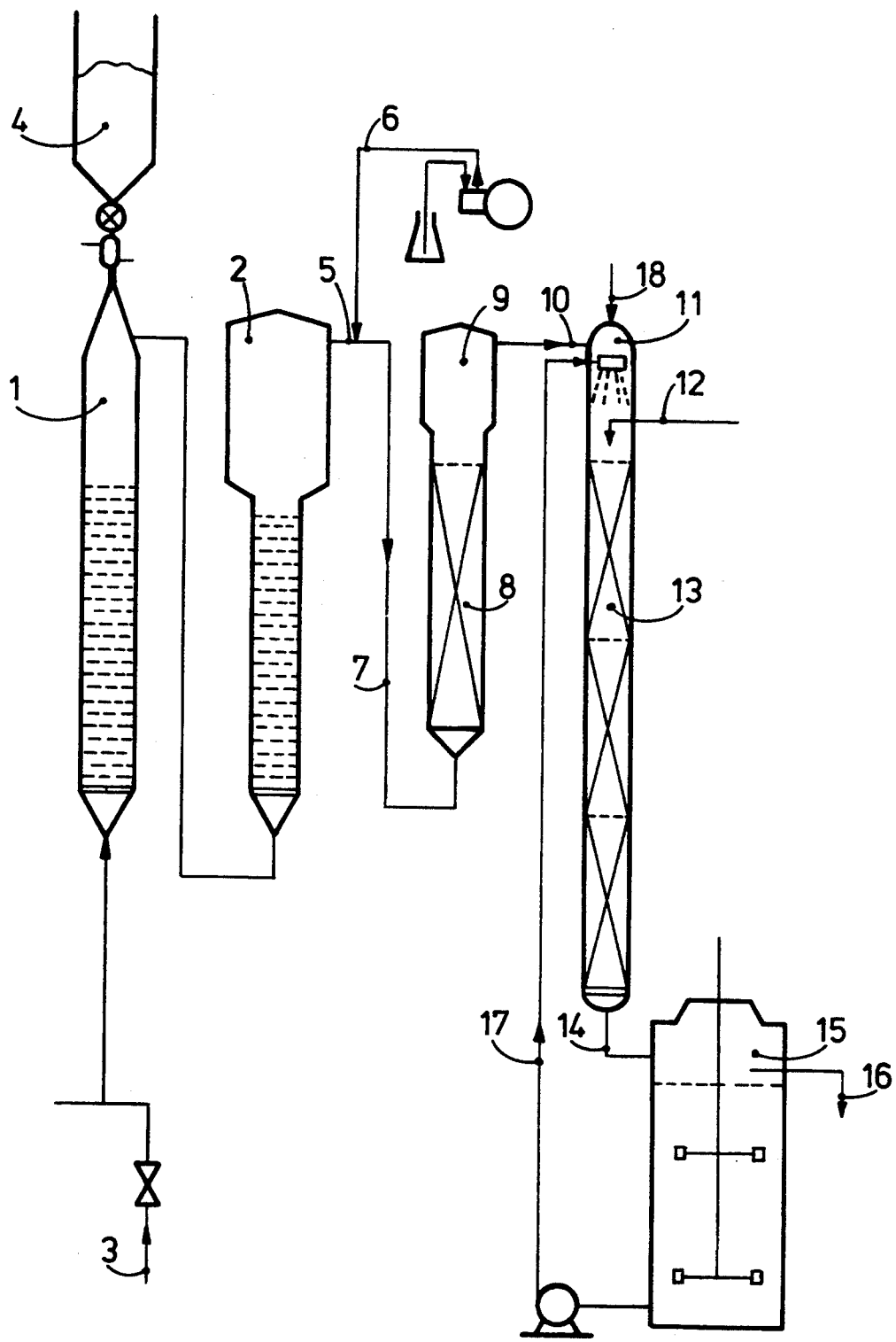

United States Patent [19]
van de Moesdijk et al.

[11] Patent Number: 5,350,849
[45] Date of Patent: Sep. 27, 1994

[54] PROCESS FOR THE PREPARATION OF MELAMINE FROM UREA

[75] Inventors: Cornelis G. M. van de Moesdijk, Beek; Hendrik J. Janssen, Sittard; Josephus C. Schroijen, Landgraaf, all of Netherlands

[73] Assignee: DSM N.V., Heerlen, Netherlands

[21] Appl. No.: 66,175

[22] PCT Filed: Nov. 28, 1991

[86] PCT No.: PCT/NL91/00240
 § 371 Date: Jun. 1, 1993
 § 102(e) Date: Jun. 1, 1993

[87] PCT Pub. No.: WO92/09585
 PCT Pub. Date: Jun. 11, 1992

[30] Foreign Application Priority Data
Nov. 29, 1990 [NL] Netherlands .......................... 9002606

[51] Int. Cl.$^5$ .................... C07D 251/62; C07D 251/60
[52] U.S. Cl. ...................................... 544/203; 544/201
[58] Field of Search .................................. 544/203, 201

[56] References Cited

U.S. PATENT DOCUMENTS

3,386,999  6/1968  Manes ............................. 260/249.7
3,414,571 12/1968  Haines ............................ 260/249.7

FOREIGN PATENT DOCUMENTS

0051156  5/1982  European Pat. Off. .
8105027  6/1983  Netherlands .

*Primary Examiner*—John M. Ford
*Attorney, Agent, or Firm*—Cushman, Darby & Cushman

[57] ABSTRACT

The invention relates to a selective removal of impurities from the gas stream leaving a melamine synthesis reactor in the preparation of melamine from urea by means of a treatment with steam at elevated temperature in the presence of a catalyst which is shape-selective. For instance a molecular sieve is chosen.

11 Claims, 1 Drawing Sheet

PROCESS FOR THE PREPARATION OF MELAMINE FROM UREA

The invention relates to the steam treatment of the gas stream leaving the synthesis reaction in the preparation of melamine from urea or the thermal decomposition products therefrom.

Such steam treatment is disclosed in U.S. Pat. No. 3,386,999 and has the object of producing, after quenching of the treated gas stream, highly pure melamine which is free of cyanic acid and other melamine precursors. In the single example of this patent publication the gas stream leaving the synthesis reactor is treated with steam for an unspecified period of time, the melamine obtained after a quenching and crystallisation is characterised by "dry and pure". Only 253.0 kg/hours melamine are obtained from 790 kg urea-feed per hour. A same process is described in U.S. Pat. No. 3,414,571: The gas stream leaving the synthesis reactor is treated with steam only. Further NL-A-8105027, example 3 discloses that under the practical conditions of conventional melamine synthesis processes, temperature 360°–400° C., and contact time 0.1–2.0 seconds, the conversion of cyanic acid is small if no catalyst is present and the uncatalysed process of U.S. Pat. No. 3,386,999 is of no practical use. Therefore NL-A-8105027 proposes the use of a catalyst in the steam treatment to decompose gaseous urea, thermal decomposition products thereof and melamine containing gas streams into carbondioxide and ammonia. Preferred catalysts are chosen from the group of active carbon, oxides and phosphates of boron and aluminum. EP-A-51156 claims the use of iron and copper oxide to catalyze the steam treatment of gas stream containing melamine, cyanic acid etc. At temperatures in the range 100°–150° C. a virtually complete conversion of HCN, melamine and isocyanic acid into ammonia and carbon dioxide is realized.

These known catalytic treatments make only sense when all or virtually all of the above-mentioned compounds are to be removed from off-gas streams. In practice, however, there appears to be a demand for selective removal of HCN, isocyanic acid, cyanamide and similar compounds from process gas streams still containing melamine in higher concentrations without significant amounts of melamine being converted. This applies, for instance, to the product stream leaving the synthesis reactor in the melamine process. This stream contains in the fluidizing gas, ammonia, the carbon dioxide and ammonia released in the reaction, besides higher concentrations of melamine product and, to a much lesser degree, isocyanic acid, cyanamide and any hydrogen cyanide formed. When melamine is recovered from the process stream by cooling with water, an aqueous medium or a cold gas stream, these compounds give rise to the formation or precipitation of undesirable by-products such as ureido melamine, melam, melem, cyanuric acid, melamine cyanurate, ammelide, guanidine and ammeline. These contaminate either the sublimated melamine or the melamine-containing suspension, and as a consequence either melamine of too low purity is obtained, or a further purification step, for instance by recrystallization, as disclosed in U.S. Pat. No. 3,496,177, becomes necessary. It may also prove necessary to prevent the build-up of impurities in the aqueous process stream obtained after separation, for instance by filtration, of the melamine, as this restricts recycling of this aqueous process stream in the process (see for instance U.S. Pat. No. 44,084,046). For the several variants of the known melamine synthesis processes and the gas and liquid streams occurring in these, the general process literature is referred to as well as the many patent applications relating to this literature, for instance U.S. Pat. No. 3,321,603, 3,300,493, 3,513,167, 3,700,672, 4,348,520 and GB-A-1309275. The abovementioned restrictions raise the costs or necessitate the discharge of streams with a relatively high environment-burdening effect.

It is therefore the object of this invention to obtain a process for the treatment of gaseous product streams containing isocyanic acid, cyanamide and similar compounds in the preparation of melamine in which these compounds under the practical conditions of the process are converted into non-interfering by-products without melamine being decomposed to any significant degree.

The non-catalytic hydrolysis treatment being too slow, and the known catalyzed processes being non-selective, the inventors nevertheless have succeeded in developing a catalytic hydrolysis process that selectivity converses cyanic acid and other precursors of melamine into carbon dioxide and ammonia without appreciably converting melamine, even though the latter may be present in a more than 1000-fold excess.

The process of the invention for treatment of a gas stream in the preparation of melamine from urea or from thermal decomposition products of urea which gas stream is the product stream leaving the synthesis reactor, which gas stream is treated with steam, at a temperature between 100° and 500° C., before recovery of melamine comprises that the gas stream is treated with steam in the presence of a shape selective hydrolysis catalyst which catalyst has micropores with an effective diameter of between 0.3 and 2.0 nm and in which at least 50% of the active sites of the catalyst are located within the micropores.

Shape-selective catalyst means in this respect, that the shape of the catalyst is such that its active sites are better assescible to molecules to be hydrolyzed than those that are not.

Shape selectivity of a catalyst is mainly determined by two factors, i.e. (1) the total number and location of catalytically active sites, and (2) the get-at-ability of the different reactants to these locations. Complete specificity of the hydrolysis can in principle be realized if the catalytically active sites are located in such a way that they are only accessible for the by-products to be hydrolysed. This would be the case if the catalytic sites are located at the inner surface of the catalyst only, and the melamine molecules are prevented of entering the inner surface of the catalyst.

Generally the "inner" surface of the catalyst is defined as the active surface located in the micropoxes of the catalyst and the outer surface as the active surface located in the mesopores of the catalyst. The diameter of the micropores are between 0.3 nm and 2.0 nm, preferably smaller than 1.2 nm and even more preferably smaller than 1.0 nm. Highest selectivity can be attained if the micropores are smaller than 0.8 nm. However pores with a diameter less than about 0.4 nm do not participate in the hydrolysis process.

The catalytic active surface should be located mainly in the micropores i.e. at least 50% of the active sites are located within the micropores. Preferably less than 1/6 of the active sites is located in the mesopores, more preferably this fraction is smaller than ⅛, best results are obtained if this fraction is smaller than 1/10.

The above requirements with respect to pore diameter and active site location are indicative for catalysts that in principle are usefull as shape selective catalyst, however in the practice of industrial processes transport phenomena can play an important role, and selectivity may be affected by catalyst particle sizer and the methods (for instance sintering or pressure) and materials (binders) used in shaping the catalyst into granulate, beads, spheres etc. for practical use in large scale processes. (Micro)pores with inert surfaces may be introduced and other pores (partly) obstructed, thereby influencing the get-at-ability of the active sites. Therefore catalysts having similar micropore diameter and distribution of active sites over inner and outer surface may show a different selectivity.

It is preferred that the process of the present invention is performed under such conditions that at least 60%, more preferably at least 80% and most preferably at least 90% of the by-product, but that at most 10%, more preferably at most 5% and most preferably at most 3% of the melamine in the gas stream is converted into carbondioxide and ammonia.

The catalyst for the hydrolysis reaction of melamine and by-products should contain acid cites. Oxidic materials are very usefull as hydrolysis catalyst. Zeolites and molecular sieves are especially usefull as shape selective catalyst material, as these show micropores with well defined diameters.

The invention will now further be elucidated by the example of zeolites, however the invention is not limited thereto, and every material possessing acidic active groups that is or can be brought into a shape selective form forms part of the invention.

Zeolites are naturally occurring or synthetically produced crystalline alkali metal alumino-silicates with a three-dimensional interconnecting network of structure of silica and alumina tetrahedra and form part of the state of the art of catalysis. Examples are mordenite and erionite and the A-type zeolite, which basically is in the sodium form. Zeolites are commercially available and can be obtained in many forms. Zeolites are normally characterized by their nominal pore diameter. This is the pore opening that can be calculated on the basis of the crystallography of the zeolite. However there are generally inhomogenities and other factors disturbing the regular crystallographic structure. Therefor the effective pore diameter should be preferred to characterize the zeolite for practical reasons. The effective pore diameter is the diameter of the largest inert molecules that still enter the cavities in the zeolite structure. This parameter is normally determined by measuring the absorption of small model molecules as funtion of their molecular diameter.

However this measurement being indicative for the determination of the actual micropore diameter distribution in the catalytic material, does not give the information about the number of the active sites in the micropores vs. those outside thereof.

The inventors have found that the use of temperature programmed desorption (TPD) of trialkylamine molecules is a representative method for determining the available number of active sites and the distribution of the active sites over inner and outer surface of inorganic catalyst. In TPD a catalyst sample is at room temperatures equilibrated with the vapour of the trialkylamine. Consequently the temperature is increased gradually to about 500° C., and the weight loss as a function of the temperature is determined. The weight of adsorbed trialkylamine at 100° is taken as indication of the number of acid sites that are accecsible to the amine. If the TPD measurements are performed with ammonia (radius 0.3–0.4 nm) and triethylamine (radius about 0.8 nm), the number of acid sites accessible to the small by-product molecules and those accessible to melamine respectively are determined.

The catalyst's selectivity is further improved when the active groups on the outer surface of the catalyst are deactivated. This can be achieved by various known processes. Examples are inertization by ion exchange, loading with inert metals, for instance gold, or with inert groups, for instance silicon compounds such as $SiCl_4$, tetraalkyl orthosilicate, etc. The use of tetraethyl orthosilicate is preferred.

Depending on the technological conditions, such as reactor type, temperature and gas load, the catalyst can be applied in the form of powder, tablets, rings, spheres, rods, etc. of varying diameters, The temperature and pressure at which the conversion according to the invention is applied may vary within very wide limits, for instance 100°–500° C. and 0.1–100 bar, and are determined mainly by the temperature and pressure of the gas stream supplied, so that in most cases they will depend on the melamine synthesis process and the place in the process where the conversion is initiated. The lower limit of the temperature range is formed for practical reasons by the desublimation point of the melamine in the gas stream. Very high temperatures, for instance more than 425° C., should generally be avoided to prevent depolymerization of melamine in cyanamide.

To achieve a high selectivity of the conversion the amount of water is chosen so that the ratio between water and compounds to be converted is approximately stoichiometric. Generally, a steam excess promotes complete removal of the substances to be converted, but its disadvantage is that melamine may also be hydrolysed. Preferably, therefore, the steam excess is limited to approximately a three-fold excess. When there is a steam deficiency, of course not all impurities are converted. However, depending on the concentration of the compounds to be converted relative to the melamine concentration, if desired a higher or lower excess of water may be present in the gas stream or may be dosed. If only relatively very low concentrations of substances to be converted are present, the excess may be relatively high because in that case in an absolute sense only little melamine can be converted with the residual steam. It should be noted that in most cases the stoichiometric amount of steam cannot exactly be calculated because it is not possible to establish unequivocally the identity and concentration of all substances in the melamine process streams. By systematic research the average person skilled in the art will be able to determine the optimum amount of steam for a given situation.

The catalyst can be applied in fixed bed or fluidized bed, preferably a fixed bed reactor is applied to prevent attrition.

The contact time of the gas stream with the catalyst bed may vary within wide limits and is in part determined by the temperature of the treatment, the activity and amount of the catalyst. The average person skilled in the art, however, can simply establish this parameter for each individual case by systematic research. Generally, this contact time will be between 0.25 and 1.5 sec.

The invention will now be elucidated with reference to the following examples, without being limited thereto.

EXAMPLES

In a laboratory set-up the melamine synthesis was carried out at atmospheric pressure, subsequently the gas stream leaving the melamine synthesis reactor was subjected to the hydrolysis according to the invention and the melamine was recovered from the gas stream in a quench section as substantially depicted in FIG. 1. The synthesis section comprises two series-arranged fluidized bed reactors (1) and (2) of approximately 300 and 700 cm$^3$, with a catalyst bed cross section of 7 and 12.5 cm$^2$, respectively. Both reactors contained 80 g of a customary SiO$_2$—Al$_2$O$_3$ catalyst. As fluidization medium ammonia (3) was fed through the bottom plate of the first reactor. Urea (4) was dosed in the form of prills to the bed of the first reactor (dosing of a urea melt is possible in principle). The gas stream (5) leaving the second reactor is of a composition that is representative of commercial processes with a so-called wet melamine catch. The degree of conversion from urea to melamine is of the order of 90 to 95%.

Subsequently water (6) was dosed to the melamine-rich gas stream (5) leaving the second reactor and the steam-enriched gas stream (7) was passed over a fixed catalyst bed (8), with a height of 5–15 cm, depending on the type of catalyst, and a cross section of 10 cm$^2$, into the hydrolysis reactor (9).

The gas stream (10) leaving the hydrolysis reactor was subsequently cooled very rapidly in a quench system (11) using an amount of water that allowed all melamine present to dissolve. For proper contact the liquid and the gas were passed co-currently over a packed scrubber (13) (wet catch). The solution obtained (14) was recycled (17), via a buffer vessel with a continuous drain, to this quench system. The continuous drain (16) was set so that the input and output of the entire system per unit of time were in equilibrium.

Experiments were performed using different hydrolysis catalysts at different levels of the steam supply to and the temperature of the hydrolysis reactor.

As soon as the system had stabilized, samples were taken from the buffer vessel, which were analyzed for the presence of melamine and by-products.

Of the catalysts the active surface area and its distribution over inner and outer surface were determined by means of temperature programmed desorption. The results are presented in Table 1.

The catalysts were applied as an extrudate, bead or in pellet form. The Zeolith 4A powder was mixed with 20% silica as inert binder and then tabletted.

EXAMPLES I–VIII AND COMPARISON EXPERIMENTS A AND B

The here described experiments were carried out according to the above process.

The samples were analyzed by liquid chromatography. Depending on the component to be analyzed, detection took place by the UV, fluorescence, conductivity or polarographic method.

In the experiments I–VIII the ammonia flow rate was 72 Nl/hr, and the urea flow rate 35.5 g/hr. Water flow rate and temperature were varied as indicated in the Table 2. In experiments I–V the UCAR 60343 catalyst was used. Zeolon 400 and Grace 522 were used in VI and VII–VIII respectively.

In comparison experiments A and B the urea flow rate was increased to 47.6 g/hr. As catalyst Grace 544 was used (table 3). Clearly no selectivity at all can be obtained with this catalyst of which the active sites on the inner surface are less than 50% of the total available number of active sites.

TABLE 1

| Catalyst Manufacturer | Type | Form | TPD NH$_3$ mol/g | TPD TEA mol/g | Micropore size nm |
| --- | --- | --- | --- | --- | --- |
| PG Corp. (Norton) | Zeolon 400 | extrudate | 2000 | 160 | Mordinite nom 0.4–0.8 effective 0.35 |
| Union Carbide | UCAR 60343 | extrudate | 2400 | 160 | nom 0.36–0.52 |
| Grace | 522 | bead | 3100 | 290 | Ca-alumino-silicate |
| Grace | 544 | bead | 2600 | 1380 | Nominal pore size 0.5 mm |
| Bayer | Zeolith | 4A + 20% SiO$_2$*) tablet | | | nom 0.4 |
| Norit | Active Carbon Supra A-8859 | extrudate | 250 | 3700 | na**) |

*)Zeolith 4A Supra A-8859 particles as obtained from the manufacturer were mixed with 20% (wt) highly pure and in active SiO$_2$ and compressed to tablets. It should be remarked that it is not exactly known which binder material are used by the other manufacturers. Generally these materials are alumina and or clay, of which the activity for the hydrolysis process is not to predict so that they may cause at this stage some deviations from the predicted behavior for the present shape selective catalyst.

**)It is apparent that TPD of ammonia and TEA (triethylamine) cannot be used to characterize active carbon. Further despite the high surface of active carbon the number of active sites as determined by NH$_3$—TPD is small.

TABLE 2

| Experiment | I | II | III | IV | V | VI | VII | VIII |
| --- | --- | --- | --- | --- | --- | --- | --- | --- |
| water flow rate [g/hr] | 1.14 | 2.28 | 0.57 | 1.14 | 2.28 | 1.15 | 1.14 | 1.70 |
| temperature [°C.] | 375 | 375 | 360 | 360 | 360 | 390 | 370 | 370 |
| % melamine conversion | 2 | 6 | 1 | 2 | 4 | 3.6 | 5 | 8 |

TABLE 2-continued

| Experiment | I | II | III | IV | V | VI | VII | VIII |
|---|---|---|---|---|---|---|---|---|
| reduction of impurity [%] | 84 | 91 | 82 | 84 | 91 | 67 | 90 | 94 |

TABLE 3

| Experiment | A | B |
|---|---|---|
| water flow rate [g/hr] | 1.15 | 2.30 |
| temperature [°C.] | 390 | 390 |
| % melamine conversion | 9.3 | 13.9 |
| reduction of impurity [%] | 17 | 15.7 |

Experiments III, IV and V clearly illustrate the effect of the excess of injected steam on the conversion. 0.57 g/hr steam approximately corresponds to the amount of water stoichiometrically needed at 95% urea conversion into melamine.

EXAMPLE IX AND X

In processes involving cooling of the gas stream leaving the reactor with a cold ammonia/carbon dioxide mixture in the quench section and melamine recovery by sublimation, it is possible to operate the hydrolysis reactor under even more favourable conditions by recycling a portion of the $NH_3/CO_2$ gas mixture leaving the quench section to the hydrolysis reactor and diluting the gas stream before hydrolysis, so that a lower melamine partial pressure is obtained and, without additional means, the temperature of the hydrolysis reactor can be raised to the desired level. In Examples IX and X this situation is simulated by dosing mixed gas, $NH_3:CO_2$ ratio=2:1, upstream of the hydrolysis reactor in the feed circuit (250° C.) upstream of the hydrolysis steam supply. Recycle gas of 250° C. was added to the residue gas of 390° C. from the synthesis reactor in such an amount that the temperature of the hydrolysis reactor was 355° C. (Ratio of reaction gas:recycle gas=approximately 3:1). After stationary conditions had been reached, samples from the buffer vessel were analyzed. The results are given in Table 4.

TABLE 4

| Experiment | IX | X |
|---|---|---|
| NH3 flow rate [Nl/hr] | 72 | 72 |
| urea flow rate [g/hr] | 35.5 | 35.5 |
| water flow rate [g/hr] | 1.14 | 2.28 |
| temperature [°C.] | 355 | 355 |
| % melamine conversion | 1 | 3 |
| reduction of impurity [%] | 81 | 90 |
| catalyst | UCAR 60343 | |

EXAMPLE XI AND COMPARISON EXPERIMENT C

Using the conditions of experiment IX, with Zeolith 4A as catalyst, in this example (XI) melamine separation from the process stream by desublimation was simulated, to which end a cooled rod (18) was introduced into the quench section. The same experiment was conducted while the hydrolysis reactor was bypassed (comparison experiment C). The solid samples obtained were analyzed for the most abundant impurities. The results are presented in Table 5.

TABLE 5

| Impurity | concentration, wt. % | |
|---|---|---|
| | C | XI |
| ammeline | 0.33 | <0.02 |

TABLE 5-continued

| Impurity | concentration, wt. % | |
|---|---|---|
| | C | XI |
| ammelide | 0.49 | 0.017 |
| cyanuric acid | 0.21 | 0.011 |
| cyanourea | 0.60 | 0.02 |
| cyanomelamine [ppm] | 160 | 25 |
| melem [ppm] | 460 | 10 |

EXAMPLE XII

The Zeolon 400 catalyst was treated with tetraethylorthosilicate, through adsorption at between 300° and 350° C. of the tetraethylorthosilicate from a nitrogen stream, which is saturated at 85° C. with the silicate, during a period of one hour. Consequently the treated catalyst is calcined at 500° C. in air during 2 hours. Of the treated calcined catalyst the TPD of ammonia and triethylamine is determined. The result is given in Table 6.

TABLE 6

| | $NH_3$ $10^{-6}$ mol/g | TEA $10^{-6}$ mol/g |
|---|---|---|
| Zeolon 400 (untreated) | 2000 | 160 |
| Zeolon 400 (treated) | 2120 | 89 |

The number of active sites accessible for TEA has decreased by nearly factor two, whereas the total number of active sites has remained nearly constant. Experiment VI was repeated for this example XII with the treated Zeolon 400. The melamine conversion was about 2.5% in contrast to the 3.6% according example VI. Furthermore, in example VI 67% of the impurities was converted, now 80% of the impurities was converted, showing the positive effect of deactivation of the outer surface on the selectivity of the catalyst.

We claim:

1. A process for treating a product gas stream having by-products therein from the preparation of melamine from urea in a reactor or from the thermal decomposition products of urea in a reactor, wherein said gas stream is the product stream leaving the reactor, comprising treating said gas stream with steam at a temperature of 100° C. to 500° C. in the presence of a shape-selected hydrolysis catalyst having micropores with an effective diameter between 0.3 and 2.0 nm and having at least 50% of active sites of the catalyst located within the micropores, whereby bi-products in said gas stream are converted into carbon dioxide and ammonia.

2. A process according to claim 1, wherein the catalyst is selected from the group consisting of natural zeolites, synthetic zeolites and molecular sieves.

3. A process according to claim 1, wherein at least 80% of the active sites are located within the micropores.

4. A process according to claim 3, wherein at least 90% of the active sites are located within the micropores.

5. A process according to claim 1, wherein the micropores have an effective diameter smaller than 1.2 nm.

6. A process according to claim 5, wherein the micropores have an effective diameter of less than 0.8 nm.

7. A process according to claim 1, wherein the micropores have an effective diameter greater than about 0.4 nm.

8. A process according to claim 2, wherein the catalyst has an outer surface, said outer surface containing active sites, and said active sites on said outer surface are deactivated.

9. A process according to claim 8, wherein said catalyst has been treated with tetraethylorthosilicate.

10. A process according to claim 1, wherein a process is conducted at a temperature above about 300° C.

11. A process according to claim 2, wherein in said treatment the amount of steam used is one to three times of amount of steam required for complete conversion of the byproducts in said product gas stream.

* * * * *